United States Patent
Takahashi et al.

(10) Patent No.: US 6,338,710 B1
(45) Date of Patent: Jan. 15, 2002

(54) DEVICE FOR STABILIZING A TREATMENT SITE AND METHOD OF USE

(75) Inventors: Masao Takahashi, Chigasake (JP); Elazer E. Edelman, Brookline, NJ (US); Kenneth W. Carpenter, Del Mar, CA (US)

(73) Assignee: MediVas, LLC, La Jolla, CA (US)

( * ) Notice: Subject to any disclaimer, the term of this patent is extended or adjusted under 35 U.S.C. 154(b) by 0 days.

(21) Appl. No.: 09/293,334

(22) Filed: Apr. 16, 1999

Related U.S. Application Data

(63) Continuation-in-part of application No. 09/171,774, filed as application No. PCT/JP97/04230 on Nov. 20, 1997, now Pat. No. 6,071,295.

(30) Foreign Application Priority Data

Feb. 27, 1997 (JP) .............................................. 9-44317

(51) Int. Cl.[7] ................................................. A61F 2/00
(52) U.S. Cl. ........................................ 600/37; 128/897
(58) Field of Search ................................ 606/190, 191, 606/193, 123, 166, 213; 600/37, 235, 201, 204, 207, 208; 128/897

(56) References Cited

U.S. PATENT DOCUMENTS

| 3,720,433 A | 3/1973 | Rosfelder ..................... 294/64 |
| 3,858,926 A | 1/1975 | Ottenhues ..................... 294/64 |

(List continued on next page.)

FOREIGN PATENT DOCUMENTS

| DE | G 90 04 513.0 | 8/1990 | |
| EP | 0 336 065 | 2/1989 | .............. A61F/9/00 |

(List continued on next page.)

OTHER PUBLICATIONS

Fanning et al., "Reoperative Coronary Artery Bypass Grafting Without Cardiopulmonary Bypass," *The Annals of Thoracic Surgery*, 55:486–489 (1993).

(List continued on next page.)

*Primary Examiner*—Cary E. O'Connor
(74) *Attorney, Agent, or Firm*—Gray Cary Ware & Freidenrich; June M. Learn

(57) ABSTRACT

The present invention provides a flexible suction body and method of its use for temporarily immobilizing a local area of tissue during surgery or a diagnostic procedure. The invention device and method are particularly well suited for immobilizing a local area of heart tissue to thereby permit surgery, for example, minimally invasive or micro-surgery, on a coronary vessel without significant deterioration of the pumping function of the beating heart. The invention suction device, which is coupled to a vacuum source, has a ring- or horseshoe-shaped suction channel with a flexible, spreadable outer rim that flattens and spreads outwardly against the surface of the treatment site as air is withdrawn from the suction channel. This design distributes the pressure of the suction body against the treatment site while maximizing the suction field to minimize bruising and suction hemorrhage at the treatment site caused by the suction body. In one embodiment, the suction body is sized for attachment to the tip of a hollow endoscopic catheter, with the hole in the center of the suction body being mounted around the periphery of the hollow catheter tip and allowing for passage from the catheter into the treatment site of a needle, or trocar for injecting materials such as drugs or genetic constructs into the treatment site or for piercing a treatment site, such as a solid tumor, to remove fluid or tissue therefrom for diagnosis. The suction body is preferably manufactured of a soft, compliant material, such as an elastomeric polymer, to conform to the surface of the heart and may be contoured in overall shape to further enhance its conformation to a contoured surface, such as the surface of the heart.

41 Claims, 3 Drawing Sheets

U.S. PATENT DOCUMENTS

| | | |
|---|---|---|
| 4,047,532 A | 9/1977 | Phillips et al. |
| 4,048,990 A * | 9/1977 | Goetz ............................ 128/64 |
| 4,368,736 A | 1/1983 | Kaster ......................... 128/334 |
| 4,627,421 A | 12/1986 | Symbas et al. ................ 128/20 |
| 4,637,377 A | 1/1987 | Loop ............................ 128/1 R |
| 4,646,747 A | 3/1987 | Lundback .................... 128/643 |
| 4,718,418 A | 1/1988 | L'Esperance, Jr. ........ 128/303.1 |
| 4,736,749 A | 4/1988 | Lundback .................... 128/643 |
| 4,766,907 A | 8/1988 | de Groot et al. ............. 128/754 |
| 4,808,163 A | 2/1989 | Laub ........................... 604/105 |
| 4,854,318 A | 8/1989 | Solem et al. ................ 128/346 |
| 4,865,019 A | 9/1989 | Phillips ........................ 128/20 |
| 4,962,758 A | 10/1990 | Lasner et al. .................. 128/41 |
| 4,989,587 A | 2/1991 | Farley ........................... 128/20 |
| 4,991,578 A | 2/1991 | Cohen .......................... 128/419 |
| 5,009,660 A | 4/1991 | Clapham ..................... 606/166 |
| 5,011,469 A | 4/1991 | Buckberg et al. ............... 604/4 |
| 5,053,041 A | 10/1991 | Ansari et al. ................ 606/148 |
| 5,108,412 A | 4/1992 | Krumeich et al. .......... 606/166 |
| 5,119,804 A * | 6/1992 | Anstadt ........................ 128/64 |
| 5,151,086 A | 9/1992 | Duh et al. ..................... 604/51 |
| 5,167,223 A | 12/1992 | Koros et al. .................. 128/20 |
| 5,171,254 A | 12/1992 | Sher ............................ 606/166 |
| 5,190,050 A | 3/1993 | Nitzche ........................ 604/164 |
| 5,287,861 A | 2/1994 | Wilk ............................ 128/898 |
| 5,365,921 A | 11/1994 | Bookwalter et al. ........... 128/20 |
| 5,372,124 A | 12/1994 | Takayama et al. .............. 128/4 |
| 5,374,277 A | 12/1994 | Hassler ........................ 606/207 |
| 5,420,698 A | 5/1995 | Suzuki et al. ................ 358/474 |
| 5,425,705 A | 6/1995 | Evard et al. .................... 604/28 |
| 5,437,651 A | 8/1995 | Todd et al. .................. 604/313 |
| 5,441,507 A | 8/1995 | Wilk ............................ 606/139 |
| 5,472,438 A | 12/1995 | Schmit et al. ................... 606/1 |
| 5,509,890 A | 4/1996 | Kazama ........................ 600/37 |
| 5,545,123 A | 8/1996 | Ortiz et al. .................. 600/235 |
| 5,569,280 A | 10/1996 | Kamerling ................... 606/166 |
| 5,571,074 A * | 11/1996 | Buckman, Jr. et al. ..... 606/191 |
| 5,613,937 A | 3/1997 | Garrison et al. ............. 600/201 |
| 5,626,609 A | 5/1997 | Zvenyatsky et al. ........ 606/208 |
| 5,727,569 A | 3/1998 | Benetti et al. ............... 128/898 |
| 5,766,164 A * | 6/1998 | Mueller et al. ................ 606/15 |
| 5,782,746 A | 7/1998 | Wright ......................... 600/37 |
| 5,782,860 A | 7/1998 | Epstein et al. .............. 606/213 |
| 5,836,311 A | 11/1998 | Borst et al. .................. 128/897 |
| 5,846,183 A | 12/1998 | Chilcoat ...................... 600/136 |
| 5,865,730 A * | 2/1999 | Fox et al. .................... 600/228 |
| 5,875,782 A | 3/1999 | Ferrari et al. ................ 128/898 |
| 5,885,271 A | 3/1999 | Hamilton et al. ............... 606/1 |
| 5,888,247 A | 3/1999 | Benetti ......................... 623/66 |
| 6,019,722 A * | 2/2000 | Spence et al. .............. 600/210 |

FOREIGN PATENT DOCUMENTS

| | | | |
|---|---|---|---|
| EP | 0 357 338 A2 | 8/1989 | |
| EP | 0 791 329 A1 | 2/1997 | ........... A61B/17/00 |
| GB | 2 214 428 A | 1/1988 | ........... A61B/19/00 |
| WO | WO 94/18881 | 9/1994 | ............ A61B/1/00 |
| WO | WO 95/01757 | 1/1995 | ........... A61B/19/00 |
| WO | WO 95/15715 | 6/1995 | ............ A61B/8/12 |
| WO | WO 95/17127 | 6/1995 | ........... A61B/17/11 |
| WO | WO 96/00033 | 1/1996 | ........... A61B/17/00 |
| WO | WO 98/37814 | 9/1998 | |

OTHER PUBLICATIONS

Th. Lavergne et al., "Transcatheter Radiofrequency Ablation of Atrial Tissue Using a Suction Catheter," *PACE*, 12:177–186 (1989).

Trapp and Bisarya, "Placement of Coronary Artery Bypass Graft Without Pump Oxygenator," *The Annals of Thoracic Surgery*, 19(1):1–9 (1975).

\* cited by examiner

DEVICE FOR STABILIZING A TREATMENT SITE AND METHOD OF USE

RELATED APPLICATIONS

This application is a continuation-in-part application of U.S. patent application Ser. No. 09/171,774, filed Oct. 26, 1998, now U.S. Pat. No. 6,071,295, which derives priority from PCT Application No. JP97/04230, filed on Nov. 20, 1997, and which is incorporated herein in its entirety by reference.

FIELD OF THE INVENTION

The present invention generally relates to surgery on body tissues and organs. More specifically, the present invention relates to a method and apparatus for temporarily immobilizing a local area of tissue subject to motion, such as the heart wall, which permits a treatment procedure to be performed on that local area of tissue.

BACKGROUND OF THE INVENTION

Coronary artery disease remains the leading cause of morbidity and mortality in Western societies and is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue, including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally involves opening the chest by median sternotomy, spreading the left and right rib cage apart; and opening the pericardial sac to achieve direct access to the heart. Next, a blood vessel or vessels for use in the graft procedure are mobilized from the patient. This usually entails mobilizing either a mammary artery or a saphenous vein, although other graft vessels may also be used.

Commonly, a heart-lung or cardiopulmonary bypass is performed so that the beating of the heart can be stopped during the surgical procedure. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations Once cardiac arrest is achieved, a graft (or grafts) is attached to the relevant portions of a coronary artery (or arteries) followed by weaning from the cardiopulmonary bypass, restarting the heart, and decannulation. Finally the chest is closed.

However, use of the cardiopulmonary bypass may create difficulties for the patient and increase the expense and time required for the procedure. In a cardiopulmonary bypass, all the patient's blood, which normally returns to the right atrium, is diverted to a system which supplies oxygen to the blood, removes carbon dioxide, and returns the blood, at sufficient pressure, into the patient's aorta for further distribution into the body. Generally, such a system requires several separate components, including an oxygenator, several pumps, a reservoir, a blood temperature control system, filters, and flow, pressure, and temperature sensors.

Problems may develop during cardiopulmonary bypass due to biological reaction of the blood to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. The anticoagulant may, in turn, increase the risk of hemorrhage. Finally, cardiopulmonary bypass sometimes necessitates administering additional blood to the patient. The additional blood, if from a source other than the patient, may expose the patient to blood borne diseases.

Due to the risks incurred during cardiopulmonary bypass, others have attempted to perform a coronary artery bypass graft procedure without cardiac arrest and cardiopulmonary bypass in a procedure known as an "off pump coronary artery bypass" (OPCAB) procedure. For example, Trapp and Bisarya (*Annals Thorac. Surg.* 19(1):1–9, 1975), immobilized the area of the bypass graft by encircling sutures deep enough to incorporate enough muscle to suspend an area of the heart while preventing damage to the coronary artery. More recently, Fanning et al (*Annals Thorac. Surg.* 55: 486–489, 1993) reported immobilizing the area of the bypass graft with stabilization sutures.

While these attempts have achieved some success, they generally require enhanced skill of the surgeon to properly create the anastomosis because, even with use of sutures to suspend a portion of the surface of the heart upon which the surgery is conducted, the beating heart continues to move in the relevant area more than desired. In addition, the sutures may cause a myocardial tear, an injury of the coronary artery branches, or such complications as embolism or focal arteriosclerosis resulting from the pressures of the ligatures upon the artery.

In order to solve such problems associated with the use of sutures to stabilize the site of an anastomosis upon the surface of a beating heart, a device known as a "local myocardial compression device" has been developed wherein myocardial portions on both sides of the coronary artery on which anastomosis is to be performed are compressed with two-tined fork-like instrument to apply pressure upon the artery and the heart itself so as to stabilize the treatment site. While use of this device has met with some success, the application of local compression to the heart can effect considerable local deterioration of cardiac function, particularly when cardiopulmonary bypass is not used to supplement blood circulation. In addition, this device does not address the problem of bleeding from a locally dissected coronary artery intended for anastomosis.

To address the undesirable effect of compression of the heart, such as is caused by use of the local myocardial compression device, a suction-assisted device has been developed having two paddles, each of which includes a series of suction ports located at the point where the device interfaces with the surface of the heart as described in U.S. Pat. No. 5,836,311. The paddles are applied to the surface of the heart across an arterial section intended as an anastomotic site and suction applied through the suction ports is employed to lift and hold the surface tissue of a beating heart at the anastomotic site to minimize motion of the treatment site while the heart continues to beat underneath. This device may be used in either a conventional, open-chest environment or in an endoscopic minimally invasive procedure. However, it has been discovered that application of pressure at localized points using such a device can cause suction induced hemorrhages on the surface of the heart that result in scarring of the heart.

The need for stabilization of a moveable surgical or biopsy site (i.e., a treatment site) is not limited to the case of the beating heart. Endoscopic catheters, for example biopsy and angiogenesis catheters, are known for use in connection with procedures involving removal of small tissue samples or injection of therapeutic drugs or genetically altered structures, such as for use in gene therapy. For accuracy of results, it is important that the depth of the tissue sample or injection be precisely controlled. When such endoscopic catheters are used at interior areas of the body that are subject to movement, such as the bowel or stomach, the lungs and the diaphragm, it is especially difficult to assure that the injection or tissue sampling device penetrates the target tissue to a desired or uniform depth. Such procedures could be facilitated by use of a device adapted for use at the tip of an endoscopic catheter that helps to stabilize the treatment site during such a therapeutic or diagnostic procedure.

Thus, there is a need in the art for new and better devices useful for stabilizing a surgical site, such as the surface of the beating heart, or for endoscopically stabilizing a an interior therapeutic or diagnostic treatment site.

SUMMARY OF THE INVENTION

In spite of the fact that off-pump coronary artery bypass surgery undertaken on the patient's beating heart (OPCAB) usually is successful with quick recovery of the patient and speedy return to work, many cardiovascular surgeons hesitate to perform such surgery because it requires an extremely highly-advanced skill and a special talent for avoiding the accompanying risks of complications to the coronary artery. It is an object of the present invention to provide a device to securely hold a surgical site, such as an anastomotic site on a coronary artery, relatively motionless throughout a bypass operation so that even surgeons having ordinary cardiovascular surgical skills can undertake such surgery with considerably reduced risk of complications.

It is a further object of the present invention to provide a device for holding an anastomotic site of a coronary artery motionless for an off-pump bypass operation without inviting deterioration of cardiac function during the operation caused by application of compression to the heart and without inviting scarring of the surface of the heart caused by application of the device.

It is a further object of the present invention to provide a practical device to hold an anastomotic site of the coronary artery motionless and bloodless during a bypass operation by restraining the bleeding from a dissected portion of the coronary artery for anastomosis.

Thus, it is an object of the present invention to provide a method and apparatus for temporarily immobilizing a local surgical site, such as an area of a beating heart, without requiring the use of stabilizing sutures.

It is a further object of the present invention to provide a disposable suction body for use in anastomosis of an autograph to the surface of a treatment site wherein the suction body includes a release mechanism so that the suction body can remain in place at an anastomotic site while the anastomosis is completed, and then the release mechanism can be actuated to remove the suction body from around the graft protruding from the anastomosis.

It is a further object of the present invention to provide a suction device for attachment to the tip of an endoscopic catheter for stabilizing a treatment site located at the interior of the body to facilitate injection of a drug or obtaining a tissue sample from a moving bodily part.

These and other objectives are met by the present invention, which provides a suction body and method of its use for temporarily immobilizing a local area of tissue. The invention flexible suction body comprises a suction channel containing a ring-shaped base defining an opening for exposing a treatment site, an outer flared, spreadable rim attached along the outer periphery of the base, a inner rim attached along the inner periphery of the base, a suction port for applying a partial vacuum within the suction channel, and at least one drain aperture in the suction body adapted for removing fluid from the treatment site while a partial vacuum is maintained in the suction channel. The suction device is coupled to a source of negative pressure.

In a preferred embodiment, the tip of the flared outer rim of the invention suction channel is sufficiently flexible that application of a partial vacuum to the suction body while the outer rim is in contact with the treatment site causes the outer rim to flatten and spread outwardly across the surface of the treatment site. By this means a soft edge for the suction channel is created to avoid bruising of the underlying tissue. As the spreading of the outer rim also enlarges the suction field to apply the partial vacuum over an increased tissue area, localized hemorrhage (e.g., of capillaries) caused by the suction is minimized or avoided.

The present invention further provides methods for stabilizing a treatment or treatment site utilizing the invention suction bodies. The invention method comprises placing an invention suction body upon the surface of the treatment site wherein the suction body is placed with the tip of the outer rim against the treatment site, and applying sufficient partial vacuum to the suction channel via the suction port to cause the suction body to attach to the treatment site while the outer rim flattens and extends outwardly thereby stabilizing the treatment site. In one embodiment, the suction body further comprises a detachable handle attached to the exterior of the suction body wherein the handle is formable, but can be locked into a fixed orientation with respect to the suction body. In another embodiment, the invention suction body is sized for attachment to the tip of an endoscopic catheter, such as an injection catheter or a biopsy catheter.

BRIEF DESCRIPTION OF THE DRAWINGS

The foregoing and other aspects of the present invention will best be appreciated with reference to the detailed description of the invention in conjunction with the accompanying drawings, wherein.

DESCRIPTION OF THE SPECIFIC EMBODIMENTS

The present invention provides a flexible suction body for stabilizing the surface of a treatment site made of a soft, compliant material, such as an elastomeric polymer, rather than hard plastic or rubber. Preferably, the suction body is made of a silicone, a urethane, or a mixture thereof, and the like. As the suction body is flexible, it will readily conform and cling to the shape of an uneven or contoured treatment site without application of compression on the treatment site while a partial vacuum is established and maintained within the suction channel.

The invention suction body comprises a suction channel containing a ring-shaped base defining an opening for exposing a treatment site, an outer flared, spreadable rim attached along the outer periphery of the base, an inner rim attached along the inner periphery of the base, a suction port for applying a partial vacuum within the suction channel, and at least one drain aperture in the suction body adapted for removing fluid from the treatment site while a partial vacuum is maintained in the suction channel. The suction channel has an overall shape and flexibility such that sufficient partial vacuum can be established and maintained therein to cause the suction body to fixedly cling to a treatment site when the suction body is placed and held against a treatment site while a partial vacuum is directed into the suction channel via the suction port, for example a partial vacuum in the range from about 100 mm Hg to about 600 mm Hg.

Generally, the suction body is flat in overall design rather than contoured, for example, with the base and tips of the inner and outer rims lying within planes. However, in an alternative embodiment, the suction body at the point of contact with the treatment surface can be contoured in overall shape to fit an uneven or contoured treatment site, such as the exterior of a human heart, and the like. Typical contoured shapes include convex, bowed, curved, and the like.

Preferably, the invention suction body further includes a release mechanism for opening and removing the suction body from a treatment site. The suction body is particularly adapted for attachment to an anastomotic site on the surface of a heart with the opening in the base shaped and sized to allow attachment of a coronary artery bypass graft to the anastomotic site therethrough. For example, the shape of the opening defined by the base of the suction body can be circular, elliptical, square, and the like. It is currently preferred that the base is ring-shaped, e.g., circular or elliptical. If circular, the opening generally has a diameter in the range from about 1 mm to about 25 mm, and the suction body is referred to as having the shape of a doughnut; and if elliptical, the opening generally has a shorter axis in the range from about 1 mm to about 15 mm, and a longer axis in the range from about 2 mm to about 25 mm.

Figure 7:
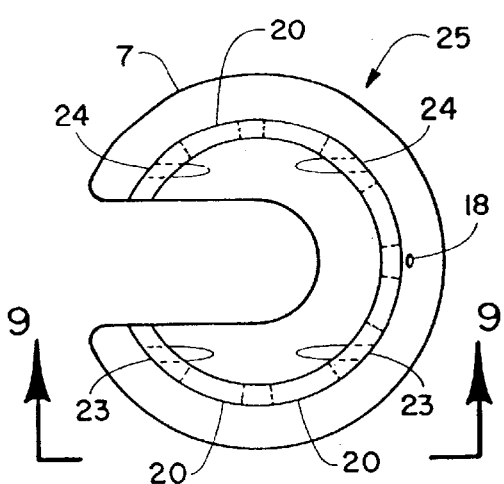
FIG. 7 is a top plan view of the horseshoe-shaped invention suction body.
Figure 8:
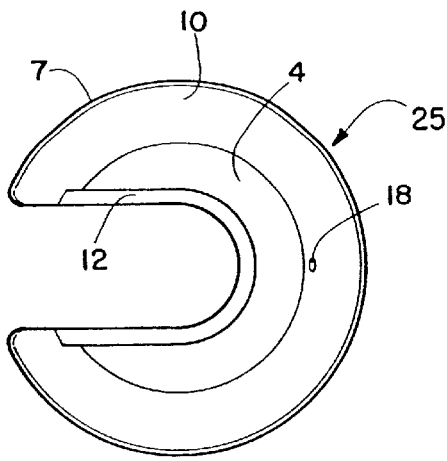
FIG. 8 is a bottom plan view of the horseshoe-shaped invention suction body.
Figure 9:
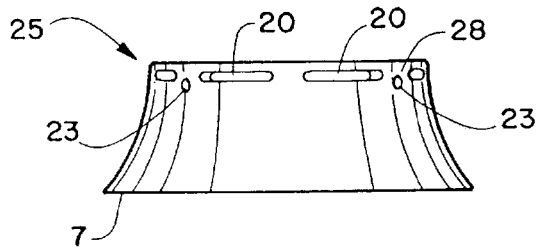
FIG. 9 is a side view drawing of the horseshoe-shaped invention suction body as viewed from arrows 9—9 in FIG. 7.

In an alternative embodiment the invention flexible suction body is in the overall shape of a horseshoe. In this embodiment the flexible suction body comprises a suction channel containing a horseshoe shaped base defining an opening for exposing a treatment site, a continuous rim running around the periphery of the base, a suction port for applying a partial vacuum within the suction channel, and at least one drain aperture in the suction body adapted for removing fluid from the treatment site while a partial vacuum is maintained in the suction channel, wherein the portion of the rim attached along the outer periphery of the base is flared, and spreadable. If the base is horseshoe shaped, the dimensions of the opening are generally similar to those created by an elliptical base, except that the ellipse is open at one end of the longer axis and the inner and outer rims of the suction channel merge around the ends of the horseshoe shape, shown as 25 in FIGS. 7–9.

To ensure that bruising or scarring caused by application of the device to the treatment site is minimized, the outer rim of the suction channel is highly flexible and compliant to the surface of the treatment site so that application of a partial vacuum to the suction body while the outer rim is in contact with the treatment site causes the outer rim to flatten and spread outwardly across the surface of the treatment site. This feature of the invention suction body is enhanced if the outer rim is substantially thinner at the tip than at the point of attachment to the base. Generally, the outer rim is graduated in thickness from the point of attachment to the base to the tip of the rim and the distance from the base to the tip is greater for the outer rim than for the inner rim so that, when the suction body is held against a treatment site with the tip of the outer rim against the treatment site and a partial vacuum is directed to the suction channel via the suction port, the suction developing in the suction channel pulls the suction body against the treatment site while the tip of the flexible outer rim flattens and spreads outwardly along the surface of the treatment site until the inner rim, which is generally less flexible and compliant than the tip of the outer rim, also comes into contact with the surface of the treatment site. This flattening and spreading of the highly flexible outer rim assures that the force of the suction body against the treatment site created by the partial vacuum with in the suction channel is distributed over a much larger area of the suction body than if the outer rim were comparatively rigid and inflexible, thereby minimizing damage to blood capillaries and tissue at the treatment site.

The flattening and spreading outwardly of the outer rim as the suction body becomes attached to the treatment site also increases the area of the suction field appreciably over what it would be if the suction body were constructed of a non-compliant material, such as a hard plastic or hard rubber. The suction field of the invention suction body is generally in the range from about 0.1 cm$^2$ to about 10 cm$^2$, for example, about 3.5 cm$^2$ to about 6.0 cm$^2$.

The increased size of the suction field compared to that of prior art devices reduces the vacuum pressure applied to a given area of tissue by a given source of partial vacuum, thereby minimizing the risk that use of the invention suction body will cause localized suction hemorrhage, for example, to capillaries in the suction field. The vacuum pressure (i.e., per area of tissue) established by the invention suction body is generally in the range from about 100 mmHg to about 600 mm Hg, and preferably about 250 mmHg to about 450 mmHg, depending upon the size of the suction field and the vacuum pressure of the source of partial vacuum. In any event, the minimal vacuum pressure is over the systolic blood pressure of the subject.

In one embodiment presently preferred wherein the suction body is ring-shaped, the suction body includes a release mechanism for opening and removing the suction body from a treatment site, for example, a groove extending partially through the suction body such that opposing forces applied to the suction body on opposite sides of the groove will cause the suction body to part at the groove for removal from the treatment site, and the like. Whatever the design of the release mechanism, it is important that the overall design of the suction body and release mechanism be such that the release mechanism does not compromise the shape and integrity of the suction channel (i.e., its ability to maintain the desired vacuum pressure within the suction channel) until the release mechanism is actuated. Inclusion of a release mechanism in a suction body having a ring-shaped base provides the advantage that the suction body can remain in place at an anastomotic site while the anastomosis is completed and then the release mechanism can be actuated to remove the suction body from around a graft that protrudes through the ring-shaped opening in the suction body.

In another embodiment, presently preferred, the invention suction body further comprises a crown located along the outer periphery of the base on the side opposite the suction channel. The crown is relatively less flexible and compliant than the outer rim and is useful for providing a support into which is placed the at least one drain aperture, and preferably a plurality of drain apertures. For example, the plurality of drain apertures in the crown can be a plurality of slots at spaced intervals. The drain apertures allow for removal of fluid (e.g. blood) from the surface of the treatment site even while the suction body is attached thereto, for example, by directing a stream of gas (e.g., compressed air) into the opening in the suction body. The ability to remove fluid from the treatment site during the surgery being conducted within the opening enhances the surgeons' vision of the treatment site. Preferably, the suction body is also transparent or translucent to further enhance visibility of the treatment site while the suction body is attached thereto.

The crown is further useful for providing a support into which are placed one or more attachments sites for attaching a detachable handle to the exterior of the suction body. In a preferred embodiment, the handle is an instrument with attaching appendages, such as is known in the art as a flexible stabilizer (available from US Surgical under the name "mini CABG™ disposable stabilizer, and the attachment sites are adapted to receive the attaching appendages of the flexible stabilizer. For example, if the attaching appendages are in the shape of a two-tined fork, the attachment sites are a plurality of apertures (e.g. drill holes) in the crown spaced for receiving the tines of the two-tined fork-like appendages on the flexible stabilizer. The detachable handle is useful for locating the suction body on a treatment site and for holding the suction body in place while the partial vacuum is directed into the suction channel and the vacuum builds up within the suction channel. In some embodiments, the handle is conformable (i.e., bendable) to assist in placing the suction body at a desired location on the treatment site, for example, on the surface of a beating heart, but can be locked into a fixed position once the suction body has been placed at a desired location. Optionally, once locked into fixed position, the handle can be temporarily attached to an exterior (e.g., stationary) object, such as an operating table or sternal or rib retractor, while suction is maintained to further stabilize the operative site and the suction body.

Figure 5:
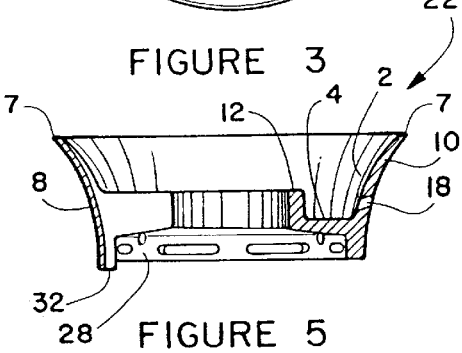
FIG. 5 is a cross-section drawing of the invention suction body taken through the section marked by arrows 5—5 of FIG. 3.

In one embodiment, the suction port is angled within the outer rim so that when the suction tube is attached thereto, the suction tube is directed away from the operative field for the convenience of the surgeons. For example, in one embodiment wherein the suction body is circular, the suction port within the outer rim is angled in two directions, to either side of a radius running through the center of the suction body, and downwardly as measured from the point of attachment of the outer rim to the base, as shown in FIG. 5. In this way, when the tube for delivering a partial vacuum to the suction port is inserted into the suction port, the portion of the suction tube that extends from the suction body is directed away from the region of space where the surgeons' hands and instruments are working.

A preferred embodiment of the invention suction body is shown in FIGS. 1–6. In this embodiment suction body 22 is circular in overall shape and suction channel 2 is constructed of circular base 4 defining a circular opening 6 for exposing a treatment site, with outer flared, spreadable rim 10 attached along the outer periphery 14 of circular base 4, inner rim 12 attached along the inner periphery 16 of base 4, and suction port 18 located in the outer rim 10. Suction port 18 is adapted to receive suction tube 46, which is in communication with a source of partial vacuum 44 (i.e., negative pressure) and through which air is withdrawn from suction channel 2 to establish a partial vacuum therein.

Crown 28, a ridge encircling the outer periphery of base 4 on the side opposite to outer rim 10, provides a location for drain apertures 20 and attachment sites 23 and 24. For convenience, attachment sites 23 and 24 are situated symmetrically with respect to suction port 18. Suction port 18 is a small drill hole (approximately 1.5 mm in diameter) adapted for receiving the end of a suction tube, such as is found in hospital operating rooms. For example, the standard suction tube available in operating rooms has an outside diameter of 10 mm and an inner diameter of 6.5–7.0 mm. An adapter as is known in the art can be used to sufficiently reduce the size of the standard tubing to establish fluid communication with the suction port in the suction body, which is generally substantially smaller. Optionally, a disposable suction reserver, such as the Medi-vac™ system (Baxter Healthcare, Deerfield, Ill.), can be interposed between the suction source and the invention suction body to capture fluids collected by the suction body.

As shown in FIG. 5, the suction port is angled to either side of a radius running through the center of the suction body, and downwardly as measured from the point of attachment of the outer rim to the base. As a result, when the suction tube 46 is attached to the suction port to direct a partial vacuum into suction channel 2, the suction tube extends from the suction body downwardly and to the side.

In this embodiment, suction channel 2 is not a complete toroidal space, but is interrupted by a reinforcing member 30 having the same height as the inner rim 12 (as measured from the base) and running between the flared outer rim 10 and the inner rim 12 along base 4. The vertical height of the flared outer rim (as measured from the plane of the base to that of the tip) is greater than that of the inner rim. The outer rim is also smoothly graduated in thickness with the point of attachment to the base being the thickest and the tip 7 being the thinnest. As further shown in FIG. 10 when the suction body is held against a treatment site with the tip 7 of the outer rim against the treatment site and a partial vacuum is directed to the suction channel via the suction port, the partial vacuum developing in the suction channel pulls the suction body against the treatment site while the tip of the flexible outer rim flattens and spreads outwardly along the surface of the treatment site until the inner rim also comes into contact with the surface of the treatment site. Therefore, when attached by suction to the surface of the treatment site, the tip of the outer rim describes generally a circle of substantially greater circumference than that described by the outer rim before its attachment to the treatment site.

Figure 3:
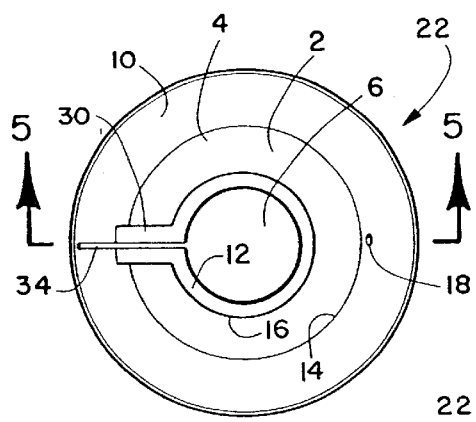
FIG. 3 is a bottom plan drawing of the invention suction body.
Figure 6:
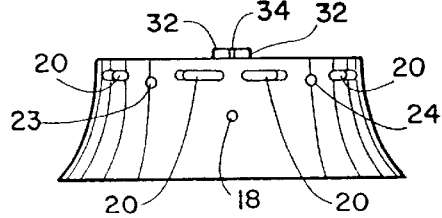
FIG. 6 is a side view drawing of the invention suction body taken through the section marked by arrows 6—6 in FIG. 2.

As shown in FIGS. 3, 5 and 6, the suction body includes a release mechanism consisting of a groove 34 having a width of about 0.25 mm to about 0.75 mm, which groove cuts through the suction body 22 and reinforcing member 30, except for a thin veneer 8 (e.g., about 0.1 mm at the point of least thickness) on the exterior of the outer rim that remains intact to preserve the integrity and shape of the suction channel. Release tabs 32 are located on the crown on either side of groove 34 and can readily be grasped by a forceps (or other functionally equivalent surgical instrument capable of applying opposite forces to the release tabs so as to cause the suction body to part at groove 34 (i.e., by breaking though the thin veneer of the outer surface of the outer rim). An invention suction body constructed of elastomeric polymer having the design and release mechanism shown in FIGS. 3, 5 and 6 maintains the integrity of the suction channel when the suction body is applied to a treatment site and a partial vacuum of up to 600 mm Hg is applied to the suction port.

Figure 1:
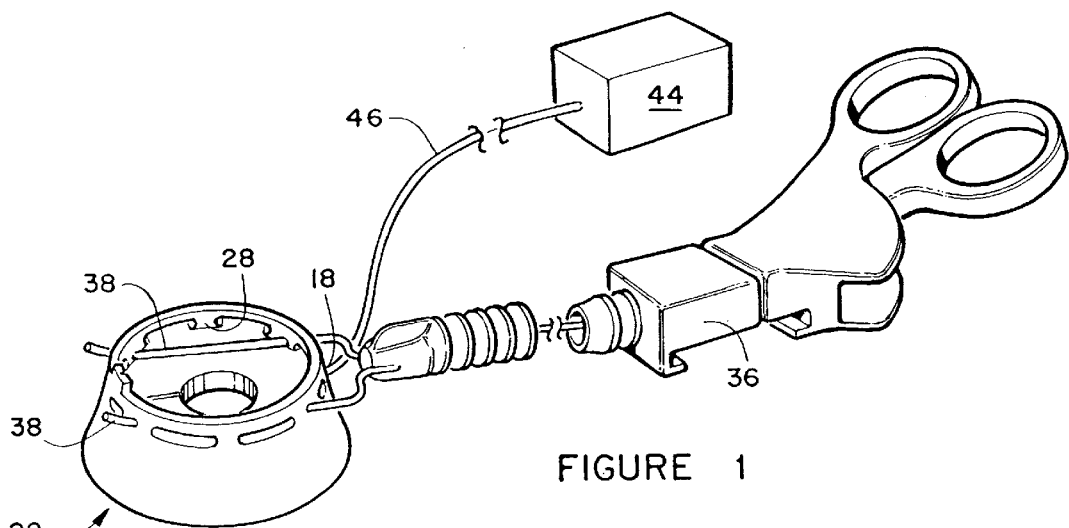
FIG. 1 is a perspective drawing showing the doughnut-shaped invention suction body mounted on the tines of a detachable handle.
Figure 2:
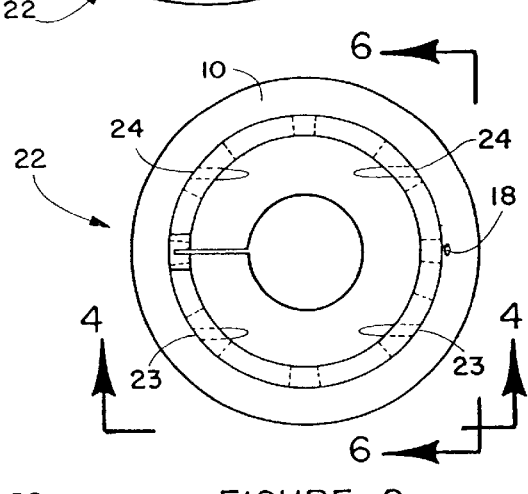
FIG. 2 is a top plan drawing of the invention suction body.
Figure 4:
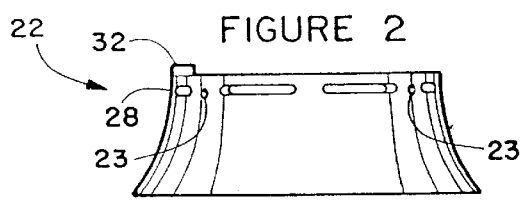
FIG. 4 is a side view of the invention suction body as viewed from arrows 4—4 of FIG. 2.

FIGS. 2, 4 and 6 show the location of attachment sites 23 and 24 in crown 28 of suction body 22 for receiving the attaching appendages of a detachable handle 36 with attaching appendages 38, shown here, respectively, as a flexible stabilizer with two attaching tines. The detachable handle attaches to the outer surface of the suction body by inserting the attaching appendages 38 into attachment sites 23 and 24. As shown here, attachment sites 23 and 24 are two sets of paired holes located in the crown with the members of each pair opposite one another so that each pair cooperatively receives one of the two tines (i.e., the attaching appendages).

Figure 11:
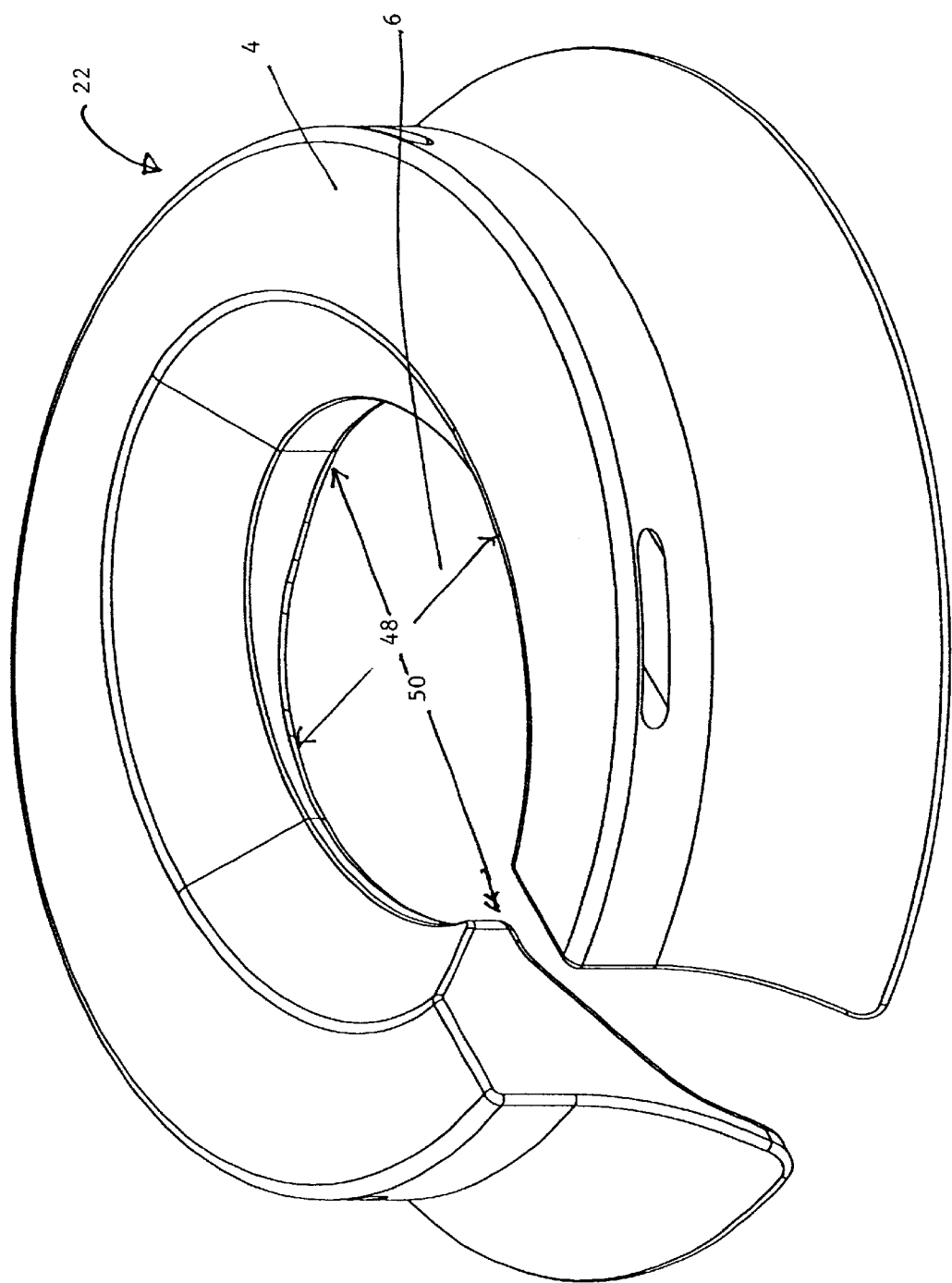
FIG. 11 is a perspective view of the elliptical-shaped invention suction body with elliptical opening.

FIG. 11 shows an embodiment of the invention suction body 22 having an elliptical base 4 defining an elliptical opening 6 with longer axis 50 and shorter axis 48 for exposing the treatment site.

In another embodiment, the invention suction body is sized and adapted for attachment to the distal tip of an endoscopic catheter, such as is used to deliver a therapeutic substance to an interior body site (e.g., a drug or gene therapy composition) or to obtain a diagnostic sample of tissue or fluid from a bodily surface, such as a solid tumor, as is known in the art. Exemplary catheters for use in connection with the invention suction device are disclosed in U.S. Pat. Nos. 4,766,907, 5,626,609, 5,151,086, 5,420,698, 5,441,507. Many such catheters have a needle or trocar slideably mounted within the distal tip of the catheter such that once the catheter is in the desired location at an interior body site, the operator can cause the needle or trocar to penetrate into the bodily surface at the treatment site either to inject a substance (e.g. a therapeutic drug) or to retrieve a substance therefrom (e.g. a solid tumor sample for histological analysis). Thus in the endoscopic suction body, the opening in the base of the suction channel is sized to passage therethrough of a needle or trocar from the interior of the endoscopic catheter into the treatment site.

In such therapeutic or diagnostic endoscopic procedures, it is important that the needle or trocar penetrate the surface of the treatment site to a precise depth. When the treatment site is a moveable interior body site, such as a heart, stomach, esophagus or lung, it is difficult to precisely control the depth of penetration of the needle or trocar into the treatment site. This problem can be overcome by attaching an appropriately sized invention suction body to the distal tip of the endoscopic catheter (e.g. with the suction tube running up the length of a lumen within the catheter) prior to insertion of the catheter into the interior body site. Once the catheter is inserted into the interior body site and the suction body is moved into contact with the desired treatment site, the vacuum is applied to the suction channel in the suction body as described herein. The suction body clings to the treatment site so as to hold the distal tip against the treatment site with sufficient stability to ensure that actuation of the needle or trocar within the endoscopic catheter will inject the drug to the desired depth or cause the trocar to obtain a sample from a predetermined depth within the treatment site. Thus, as applied to the endoscopic suction body of the invention, the term "stabilize" means that the tip of the endoscopic catheter is firmly held against the treatment site, even if the treatment site is in motion, rather than meaning that the suction body exerts sufficient control over the movement of the treatment site to actually minimize the movement of a moving treatment site.

As the negative pressure developed in the suction body is inversely proportional to the suction surface of the suction body at any given suction pressure, it can be seen that the miniature size of the invention endoscopic suction body will, however, cause a much higher suction pressure to develop within the suction body than would be suitable for use with a larger sized suction body, for example in a suction body sized for attachment to an anastomotic site on the surface of the heart. Thus, in the endoscopic suction body of the invention, the flared, spreadable outer rim is particularly useful for preventing unwanted damage to the treatment site.

The present invention further provides methods for stabilizing a treatment site utilizing the invention suction bodies. The invention methods comprise placing a suction body upon the surface of the treatment site, wherein the suction body comprises:

a suction channel comprising:
  a ring- or horseshoe-shaped base defining an opening for exposing a treatment site,
  an outer flared, spreadable rim attached along the outer periphery of the base,
  an inner rim attached along the inner periphery of the base,
  a suction port for establishing a partial vacuum within the suction channel, and
  at least one drain aperture in the suction body adapted for removing fluid from the treatment site while a partial vacuum is maintained in the suction channel,
wherein the suction body is placed with the tip of the outer rim against the treatment site, and
applying sufficient partial vacuum to the suction channel via the suction port to cause the suction body to cling to the treatment site, thereby stabilizing the treatment site. Due to the flexible construction of the suction body, especially of the outer rim, as the partial vacuum becomes established within the suction channel due to application of the partial vacuum to the suction channel, the outer rim of the suction body flattens and spreads outwardly.

In a presently preferred embodiment, the holding of the suction body is accomplished by the surgeon grasping a formable detachable handle attached to the exterior of the suction channel, such as the type of instrument that is known in the art as a flexible stabilizer (available from US Surgical under the name "mini CABG™ stabilizer." Preferably, the method further comprises locking the handle into a fixed orientation with respect to the suction body for holding while the partial vacuum is applied to the suction channel to cause the suction body to cling to the treatment site. Optionally, the handle can also be temporarily affixed to an exterior object, such as an operating table or a rib retractor, and the like, to further stabilize the suction body throughout the operation. In this preferred embodiment of the invention method, the handle attached to the suction body is not used to pull up on the treatment site because it has been discovered that pulling the treatment site away from underlying tissue places sufficient stress on a delicate treatment site to permanently damage tissue. It is a particular advantage of the invention methods that a delicate treatment site, such as the surface of a beating heart, can be stabilized using the invention suction body and methods without pulling the surface of the treatment site away from muscular contractions deeper within the underlying heart musculature.

Figure 10:
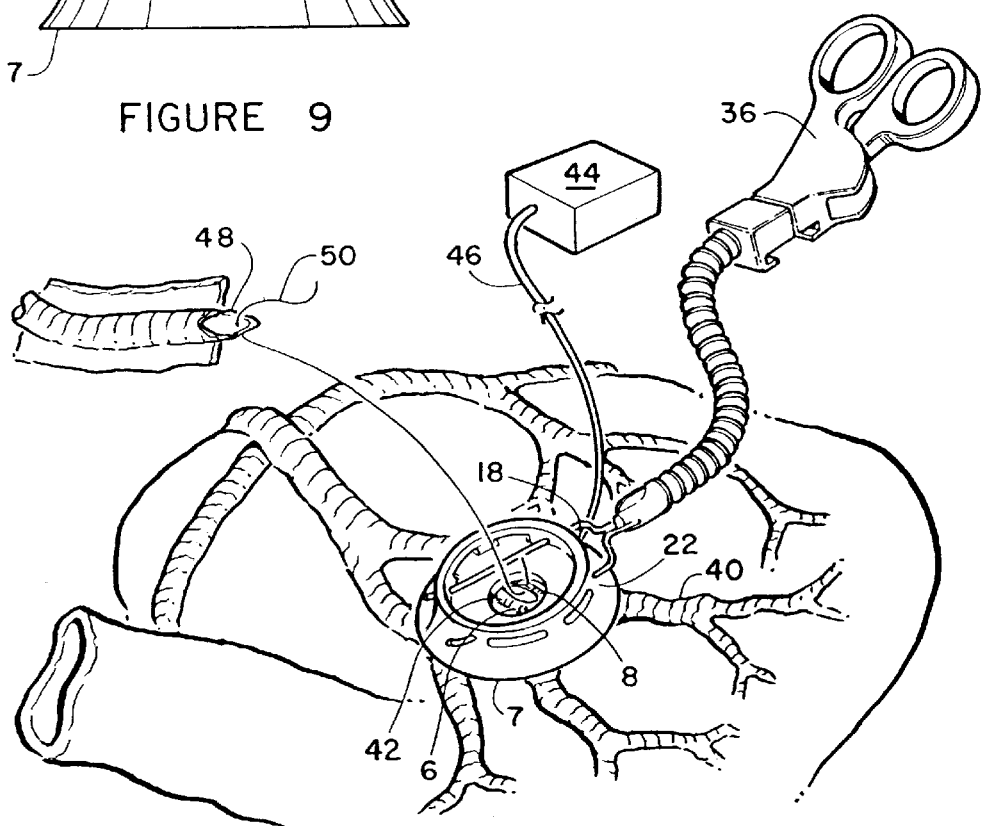
FIG. 10 is a drawing showing the invention suction body with detachable handle attached to an anastomatic site on the surface of a human heart.

The invention method is now illustrated with respect to a representative OPCAB surgery as shown in FIG. 10. First, the invention suction body 22 is positioned and held at an anastomotic site 8 of the coronary artery 40 using a detachable handle 36, shown here as a flexible stabilizer, attached to the exterior of suction body 22 in such a manner that the anastomotic site can be viewed through circular opening 6, which is surrounded by suction channel 2. Care is taken in placing the suction body that both rims of the suction channel cross over both the proximal side and the distal side of the coronary artery 40. While the suction body is held in position against the surface of the heart, a suction tube 46 attached to a suction source 44 is attached to the suction port of the suction body until sufficient partial vacuum is established in the suction channel to cause the suction body to cling to the surface of the beating heart so as to stop the blood flow in the artery within opening 8 without the need to compress the beating heart. Concurrently, the treatment site will be stably held despite the motion of the beating heart without pulling up on the handle attached to the suction body to raise the treatment site. In fact, due to the suction force applied to the treatment site by the suction body, the anastomotic site will be somewhat raised within opening 8 (i.e., partially extruded therethrough).

Next, an aperture 42 is made with a scalpel on the portion of coronary artery 40 exposed within opening 8 and an internal thoracic artery 48 (or a radial artery, inferior gastroepiploic artery or saphenous vein) is led to aperture 42 to be anastomosed to the coronary artery with a suture 50, as shown in FIG. 10. Meanwhile, internal thoracic artery 48 is occluded at a distal portion (not shown) to hamper the blood flow in artery 48 during formation of the anastomosis. When the anastomosis has been securely formed, the pressure within the suction channel is returned to atmospheric pressure, for example, by disengagement of suction tube 46 from suction port 18, and the suction body is detached from the surface of the heart and from coronary artery 40 so that blood flow in artery 40 resumes. Blood flow within internal thoracic artery 48 is also resumed, flowing through the distal side of coronary artery 40. Once blood flow has been reestablished, the release mechanism in the suction body is actuated by grasping (e.g. with forceps) release tabs 32 located on the crown 28 on either side of groove 34 as shown in FIGS. 2, 3 and 5, and applying opposite forces to the release tabs to cause the suction body to part at groove 34. The surgery ends with the final step of suturing the chest closed.

OPCAB surgery utilizing the invention suction body and methods can be performed in about 90 to 180 minutes, on average, from the thoracotomy through the suturing closed of the chest so that the fatigue of the patient as well as the burden on the surgeons and their assistants, such as the nurses, can be greatly reduced.

To further facilitate the surgery, the invention method may further comprise removing any fluid, such as blood, that accumulates within the ring-shaped opening of the suction body at the treatment site without removal of the suction body by removing such fluid through the at least one drain aperture in the suction body, for example, by applying a stream of gas to the treatment site to blow the fluid through the drain aperture and away from the treatment site.

In the invention methods, the suction body is used to apply a partial vacuum over a surface area in the range from about 0.1 $cm^2$ to about 10 $cm^2$, and preferably from about 3.5 $cm^2$ to about 6.0 $cm^2$ so as to minimize formation of localized suction hemorrhage on the surface of the treatment site.

In one embodiment of the invention methods, a suitably sized suction body according to the invention is attached to the distal tip of an endoscopic catheter, such as is used to deliver a therapy to an interior body site or to obtain diagnostic information from the body site. For example, the suction body can be used to hold the tip of a fiber optic catheter against a treatment site while a laser or other therapeutic or diagnostic light is applied to the surface of the treatment site through the opening in the base of the invention suction body. Alternatively, an invention suction body can be attached to the distal tip of a catheter having a needle or trocar slidably mounted within the distal tip of the catheter for delivering or retrieving a substance below the surface of the treatment site. Once the catheter is manipulated to place the suction body at a desired location at an interior body site and suction is applied to cause the suction body to cling to the surface of the treatment site, the operator can cause the needle or trocar to penetrate into the bodily surface at the treatment site either to inject a substance (e.g. a therapeutic drug) or to retrieve a substance therefrom (e.g. a solid tumor sample for histological analysis) site via the opening in the suction body. Because the catheter is firmly attached to the treatment site through the action of the suction body, the needle or trocar will penetrate into the treatment site for a predetermined depth of penetration even if the treatment site is located on a bodily surface that is in motion.

This embodiment of the invention methods affords the advantage that the needle or trocar from the catheter will attain a predetermined depth of penetration, thereby enhancing the reliability of the information derived from a diagnostic sample retrieved or assuring that a drug, such as an angiogenesis drug (i.e. a drug suitable for enhancing development of new blood vessels in the heart), is delivered to the most suitable depth for achieving the therapeutic goal.

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A flexible suction body for stabilizing the surface of a treatment site, said suction body comprising:

a continuous open suction channel comprising:
: a ring-or horseshoe-shaped base defining an opening for exposing a treatment site,
: an outer flared rim attached along the outer periphery of the base,
: an inner rim attached along the inner periphery of the base, and
: a suction port for establishing a partial vacuum within the suction channel, wherein the vertical distance from the base to the tip of the outer rim is greater than for the inner rim and application of a partial vacuum via the suction port while the suction body is in contact with the treatment site forms a continuous suction surface in the range from about 0.1 cm$^2$ to about 10 cm$^2$.

2. The suction body according to claim 1 wherein the suction body is ring-shaped further comprising a release mechanism for opening and removing the suction body from a treatment site.

3. The suction body according to claim 2 wherein the release mechanism comprises a groove extending partially through the suction body such that opposing forces applied to the suction body on opposite sides of the groove will cause the suction body to part at the groove for removal from the treatment site.

4. The suction body according to claim 3 wherein the groove does not compromise the integrity of the suction channel.

5. The suction body according to claim 1 wherein the treatment site is an anastomotic site on the surface of a heart and the opening in the base is sized to allow attachment of a coronary artery bypass graft to the anastomotic site therethrough.

6. The suction body according to claim 5 wherein the ring-shaped base is elliptical defining an elliptical opening in the base.

7. The suction body according to claim 6 wherein the shorter axis of the elliptical opening is in the range from about 1 mm to about 20 mm, and the longer axis of the elliptical opening is in the range from about 2 mm to about 25 mm.

8. The suction body according to claim 1 wherein the ring-shaped base is circular defining a circular opening.

9. The suction body according to claim 8 wherein the diameter of the circular opening is in the range from about 15 mm to about 20 mm.

10. The suction body according to claim 1 wherein the outer rim is graduated in thickness from the point of attachment to the base to the tip of the rim.

11. The suction body according to claim 1 wherein the base and suction channel are horseshoe-shaped.

12. The suction body according to claim 1 wherein the suction body is fabricated from an elastomeric polymer.

13. The suction body according to claim 12 wherein the elastomeric polymer is a silicone or a urethane.

14. The suction body according to claim 1 further comprising at least one attachment site for attaching a detachable handle to the outer surface of the suction body.

15. The suction body according to claim 1 further comprising a crown, wherein the crown is located along the periphery of one side of the base and the suction channel is located along the periphery of the other side of the base.

16. The suction body according to claim 15 wherein a plurality of the attachment sites are located in the crown.

17. The suction body according to claim 16 wherein the handle is a flexible stabilizer and the attachment sites are apertures in the crown for receiving the tines of a flexible stabilizer.

18. The suction body according to claim 15 wherein the suction body further comprises a plurality of drain apertures located in the crown adapted for removing fluid from the treatment site while a partial vacuum is maintained in the suction channel.

19. The suction body according to claim 1 wherein the suction body further comprises at least one drain aperture adapted for removing fluid from the treatment site while a partial vacuum is maintained in the suction channel.

20. The suction body according to claim 1 wherein the suction channel extends only partially around the periphery of the base.

21. The suction body according to claim 1 wherein the suction port is located within the outer rim.

22. The suction body according to claim 21 wherein the suction port is angled downwardly and sidewards from the point of attachment of the outer rim to the base.

23. The suction body according to claim 1 wherein the suction body is transparent or translucent.

24. The suction body according to claim 1 wherein the suction body is contoured.

25. The suction body according to claim 1 wherein the suction body is adapted for mounting at the tip of an endoscopic catheter.

26. The suction body according to claim 25 wherein the endoscopic catheter is adapted for injecting a substance into a treatment site or for removing tissue or fluid from a treatment site and wherein the opening in the base of the suction body is sized to allow passage therethrough of a needle or trocar from the interior of the endoscopic catheter into the treatment site.

27. A method for stabilizing a treatment site, said method comprising:
: a) holding a suction body against the surface of the treatment site, wherein the suction body comprises:
:: a continuous open suction channel comprising
:: a ring- or horseshoe-shaped base defining an opening for exposing a treatment site,
:: an outer flared rim attached along the outer periphery of the base,
:: an inner rim attached along the inner periphery of the base, wherein the vertical distance from the base to the tip of the outer rim is greater than the vertical distance from the base to the tip of the inner rim, and
:: a suction port for establishing a partial vacuum within the suction channel,
:: wherein the suction body is held with the tip of the outer rim against the treatment site, and
: b) applying sufficient partial vacuum to the suction channel via the suction port to form a continuous suction surface in the range from about 0.1 cm$^2$ to about 10 cm$^2$, thereby causing the suction body to cling to the treatment site so as to stabilize the treatment site.

28. The method according to claim 27 wherein the holding is by means of a formable detachable handle attached to the exterior of the suction channel.

29. The method according to claim 27 further comprising locking the handle into a fixed orientation with respect to the suction body.

30. The method according to claim 29 further comprising temporarily affixing the handle to an exterior object.

31. The method according to claim 27 wherein the stabilizing includes applying a tension to the surface of the treatment site.

32. The method according to claim 27 wherein the application of a partial vacuum causes partial extrusion of the treatment site through the opening in the base.

33. The method according to claim 27 wherein the treatment site is an anastomotic site of a coronary artery on the surface of a beating heart and the stabilizing involves substantially reducing the motion of the treatment site on the beating heart.

34. The method according to claim 27 wherein the suction body further comprises at least one drain aperture adapted for removing fluid from the treatment site while a partial vacuum is maintained in the suction channel, and the method further comprises removing fluid from the treatment site through the at least one drain aperture.

35. The method according to claim 34 wherein the removing of fluid involves application of a stream of gas to the treatment site to blow the fluid through the drain aperture.

36. The method according to claim 27 wherein the opening is sized to allow surgical manipulation of the treatment site through the opening while the suction body is attached to the treatment site.

37. The method according to claim 27 wherein the suction body further comprises a release mechanism and the method further comprises actuating the release mechanism to remove the suction body from the treatment site.

38. The method according to claim 27 wherein formation of localized suction hemorrhage on the surface of the treatment site is minimized.

39. The method according to claim 27 wherein the suction body is attached to the distal tip of a catheter and wherein the method further comprises delivering a substance to the treatment site or retrieving a substance from the treatment site via the opening in the suction body.

40. The method according to claim 39 wherein the catheter has a needle or trocar slideably disposed within the distal tip thereof such that the opening in the base of the suction body allows passage of the needle or trocar from the interior of the catheter into the treatment site for a predetermined depth of penetration and withdrawal therefrom into the catheter.

41. The method according to claim 39 wherein the treatment site is located on the surface of the heart, stomach, esophagus, or lung of the subject.

* * * * *